US007427622B2

(12) United States Patent
Zhao et al.

(10) Patent No.: US 7,427,622 B2
(45) Date of Patent: *Sep. 23, 2008

(54) METHOD OF MAKING AND USING THEAFLAVIN, THEAFLAVIN-3-GALLATE, THEAFLAVIN-3'-GALLATE AND THEAFLAVIN 3,3'-DIGALLATE AND MIXTURES THEREOF

(75) Inventors: Jian Zhao, Irvine, CA (US); Rui Zhou, Shanghai (CN); Hu Chen, Shanghai (CN)

(73) Assignee: Nashai Biotech, LLC, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/640,917

(22) Filed: Dec. 19, 2006

(65) Prior Publication Data
US 2007/0098765 A1  May 3, 2007

Related U.S. Application Data

(63) Continuation of application No. 10/601,314, filed on Jun. 20, 2003, now Pat. No. 7,157,493, which is a continuation-in-part of application No. 10/306,204, filed on Nov. 27, 2002, now abandoned.

(60) Provisional application No. 60/413,576, filed on Sep. 24, 2002, provisional application No. 60/333,515, filed on Nov. 28, 2001.

(30) Foreign Application Priority Data
Apr. 26, 2002 (CN) ................. 02 1 11512

(51) Int. Cl.
*A61K 31/353* (2006.01)
(52) U.S. Cl. .................................... 514/256
(58) Field of Classification Search ............... 514/256, 514/456
See application file for complete search history.

(56) References Cited

U.S. PATENT DOCUMENTS

| | | | |
|---|---|---|---|
| 3,228,789 A | 1/1966 | Glassman |
| 3,845,770 A | 11/1974 | Theeuwes et al. |
| 3,916,899 A | 11/1975 | Theeuwes et al. |
| 4,708,834 A | 11/1987 | Cohen et al. |
| 4,840,966 A | 6/1989 | Hara et al. |
| 4,935,243 A | 6/1990 | Borkan et al. |
| 5,318,986 A | 6/1994 | Hara et al. |
| 5,698,155 A | 12/1997 | Grosswald et al. |
| 5,879,730 A | 3/1999 | Bouwens et al. |
| 6,602,527 B1 | 8/2003 | Slaga et al. |
| 7,157,493 B2 | 1/2007 | Zhao et al. |
| 2004/0097432 A1 | 5/2004 | Roh-Schmidt et al. |

FOREIGN PATENT DOCUMENTS

DE 19627344 3/1999

WO WO 01/93886 12/2001

OTHER PUBLICATIONS

Abe et al., "Black Tea Theaflavins Are Potent Inhibitors of Squalene Epoxidase, A Key Enzyme in Cholesterol Biosynthesis," Japanese Journal of Food Chemistry, vol. 7(1), p. 47-50 (2000).
Vinson et al., "Effect of green and black tea supplementation on lipids, lipid oxidation and fibrinogen in the hamster: mechanisms for the epidemiological benefits of tea drinking," FEBS Letters 443:44-46 (1998).
Ishikawa et al., "Effect of tea flavonoid supplementation on the susceptibility of low-density lipoprotein to oxidative modification," Am. J. Clin. Nutr. 66:261-266 (1997).
Finger, "In-vitro studies on the effect of polyphenol oxidase and peroxidase on the formation of polyphenolic black tea constituents", J. Sci Food Agric, vol. 66, No. 3, 1994, pp. 293-305, XP002312128.
Patent Abstracts of Japan, 11032725, Mitsui Norin KK, Feb. 9, 1999.
Patent Abstracts of Japan, 06256180, Taiyo Kagaku Co Ltd, Sep. 13, 1994.
Chemical Abstracts, "Preparation of tea pigments for pharmaceuticals," vol. 120, No. 63, 1994, abstract No. 144138v, p. 691 col. 1, XP002312132.
Chemical Abstracts, vol. 127, No. 26, 1997, abstract No. 355154e, Meng. ME1: "Influence of theaflavin on blood lipid and hemorheologic parameters", p. 25 col. 2, XP002312133.
Chemical Abstracts, vol. 127, No. 14, 1997, abstract No. 19OO4Oz, Ishikawa, T. "Effect of tea flavonoid supplementation on the susceptibility of low-density lipoprotein to oxidative modification", p. 577, XP002312134.
Chung et al., "Mechanisms of inhibition of the Ras-MAP kinase signaling pathway in 30.7b Ras 12 cells by tea polyphenols (−)-epigallocatechin-3-gallate and theaflavin-3,3'-digallate," FASEB Journal, vol. 15, No. 11, Sep. 2001 pp. 2022-2024, XP002312129.
Hashimoto et al., "Evaluation of tea polyphenols as anti-HIV agents", Bioorganic and Medicinal Chemistry Letters, vol. 6, No. 6, 1996, pp. 695-700, XP004135008.
Yoshida et al., "Inhibitory effect of tea flavonoids on the ability of cells to oxidize low density lipoprotein", Biochemical Pharmacology, vol. 58, No. 11, 1999, pp. 1695-1703, XP002312131.
Alderman, "A Review of Cellulose Ethers in Hydrophilic Matrices for Oral Controlled-Release Dosage Forms," Int. J. Pharm. Tech. Prod. Mfr. 5(3):1-9, 1984.
Bamba et al., "Release mechanisms in gelforming sustained release preparations," Int. J. Pharm. 2:307, 1979.

(Continued)

*Primary Examiner*—Bernard Dentz
(74) *Attorney, Agent, or Firm*—Cooley Godward Kronish, LLP

(57) ABSTRACT

The present invention discloses methods of making a mixture of theaflavin, theaflavin-3-gallate, theaflavin-3'-gallate and theaflavin 3,3'-digallate, pharmaceutical compositions of the above mixture of theaflavins, diet supplement compositions of the above mixture of theaflavins and methods for using the above mixtures of theaflavin and pharmaceutical compositions thereof to treat or prevent various diseases. The present invention also discloses methods of making theaflavin, theaflavin-3-gallate, theaflavin-3'-gallate and theaflavin 3,3'-digallate, each as a separate compound, pharmaceutical compositions of the above compounds, diet supplement compositions of the above compounds and methods for using the above compounds to treat or prevent various diseases.

87 Claims, 2 Drawing Sheets

OTHER PUBLICATIONS

Figure 1:
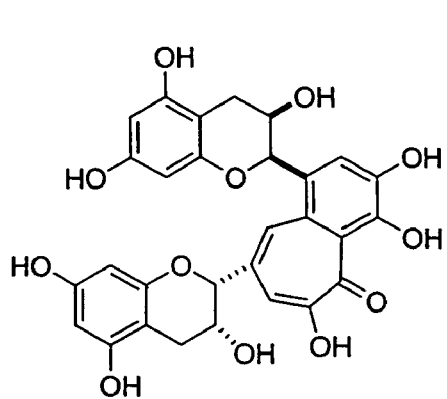
Figure 1:
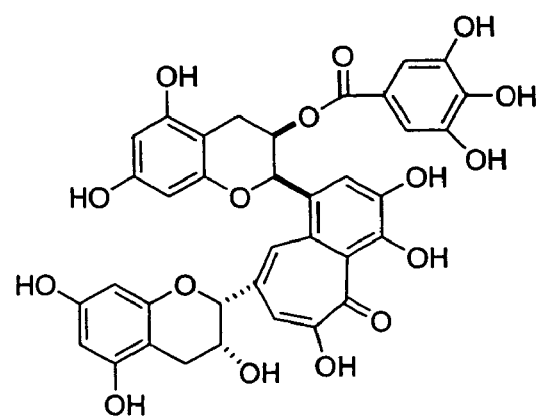
Figure 1:
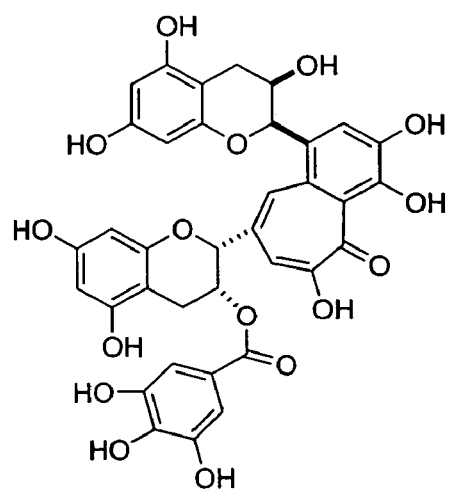
Figure 1:
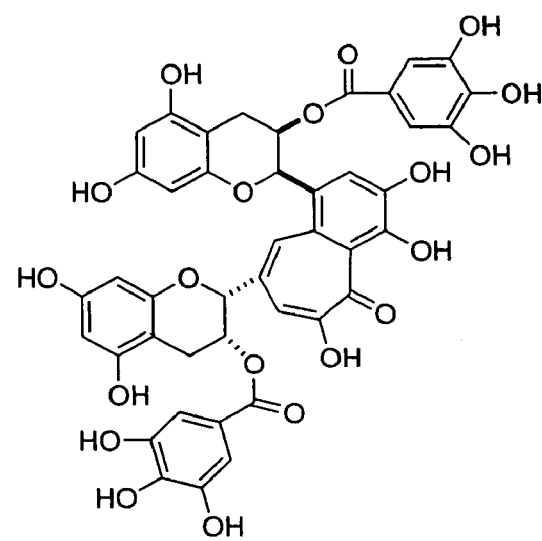

Berge et al., "Pharmaceutical Salts," J. Pharm. Sci. 66:1-19, 1977.

Leung et al., "Theaflavins in Black Tea and Catechins in Green Tea Are Equally Effective Antioxidants," J. Nutr. 131(9):2248-2251, 2001.

Sarkar et al., "Black Tea is a Powerful Chemopreventor of Reactive Oxygen and Nitrogen Species: Comparison with Its Individual Catechin Constituents and Green Tea," Biochem. Biophys. Res. Commun. 284(1):173-178, 2001.

Verma et al., "Osmotically Controlled Oral Drug Delivery," Drug Dev. Ind. Pharm. 26:695-708, 2000.

Yoshino et al., "Antioxidative Effects of Black Tea Theaflavins and Thearubigin on Lipid Peroxidation of Rat Liver Homogenates Induced by tert-Butyl Hydroperoxide," Biol. Pharm. Bull. 17(1):146-149, 1994.

"Black and Green Tea: How do they differ?", Tea Health Facts, pp. 1-4, Sep. 3, 2002, http://www.teahealth.co.uk/th/facts/1.htm.

"*Camellia sinensis* (Tea)", Biodiversity explorer, pp. 1-6, Sep. 5, 2002, http://www.museums.org.za/bio/plants/theaceae/camellia_sinesis.htm.

"Tea Polyphenols, water soluble, lipid soluble", Wuzhou International Co., Ltd., one-page, Sep. 5, 2002, http://www.chinax.com/pages/wuzhou/tea%20polyphenols.htm.

"Herbs—Green Tea (*Camellia sinensis*)", Golden Temple Ingredients-Herbs-Green Tea (*Camellia sinensis*), pp. 1-3, Sep. 5, 2002, http://www.goldentemple.com/Clients/KIIT/GT/Ingredients.nsf/Ingredients/Green+Tea+(Camellia . . . .

Eadington, "Tea Polyphenols and Cancer Prevention", Eadington/SJBR/2000, pp. 1-5, Sep. 5, 2002, http://wwwchem.csustan.edu/chem4400/SJBR/00eading.htm.

Goodsall et al., "The mechanism of theaflavin oxidation during black tea manufacture", 2nd International Electronic Conference on Synthetic Organic Chemistry (ECSOC-2), http://www/mdpi.org/ecsoc/, Sep. 1-30, 1998, pp. 1-3, http://ecsoc2.hcc.ru/DP_TOP2/dp119/dp119.htm.

Yang et al., "The Chemistry of Tea", p. 1-2, Sep. 5, 2002, http://www.teatalk.com/science/chemistry.htm.

Bhagwat et al., "Flavonoid composition of tea: Comparison of black and green teas," 1 page, USDA, Agricultural researh Services.

Diepeveen et al., "Effects of atorvastatin and vitamin E on lipoproteins and oxidative stress in dialysis patients: a randomised-controlled trial," J. Internal Medicine 257:438-445 (2005).

Yang et al., "Inhibition of growth and induction of apoptosis in human cancer cell lines by tea polyphenols," Carcinogenesis 19(4):611-616 (1998).

Dong et al., "Inhibition of Tumor Promoter-induced Activator Protein I Activation and Cell Transformation by Tea Polyphenols, (−)-Epigallocatechin Gallate, and theaflavins," Cancer Research 57:4414-4419 (1997).

Nomura et al., "Inhibition of 12-O-tetradecanoylphorbol-13-acetate-induced NF-κB activation by tea polyphenols, (−)-epigallocatechin gallate and theaflavins," Carcinogenesis 21(10):1885-1890 (2000).

Theaflavin

Theaflavin-3-gallate

Theaflavin-3'-gallate

Theaflavin-3,3'-gallate

Epicatechin

Epicatechin gallate

Epigallocatechin

Epigallocatechin gallate

METHOD OF MAKING AND USING THEAFLAVIN, THEAFLAVIN-3-GALLATE, THEAFLAVIN-3'-GALLATE AND THEAFLAVIN 3,3'-DIGALLATE AND MIXTURES THEREOF

This application is a continuation of U.S. application Ser. No. 10/601,314, filed Jun. 20, 2003, now U.S. Pat. No. 7,157,493, which is a continuation-in-part of U.S. application Ser. No. 10/306,204, filed Nov. 27, 2002 now abandoned, which claimed the benefit under 35 U.S.C. § 119(e) of U.S. Provisional Application Ser. No. 60/333,515, filed Nov. 28, 2001 and U.S. Provisional Application Ser. No. 60/413,576, filed Sep. 24, 2002 and also claimed the benefit under 35 U.S.C. § 119(a) of Chinese Patent Application Serial No. CN02111512.5, filed Apr. 26, 2002. The above applications are incorporated herein by reference in their entirety.

1. FIELD OF THE INVENTION

The present invention discloses methods of making a mixture of theaflavin, theaflavin-3-gallate, theaflavin-3'-gallate and theaflavin-3,3'-digallate, pharmaceutical compositions of the above mixture of theaflavins, diet supplement compositions of the above mixture of theaflavins and methods for using the above mixtures of theaflavin and pharmaceutical compositions thereof to treat or prevent various diseases. The present invention also discloses methods of making theaflavin, theaflavin-3-gallate, theaflavin-3'-gallate and theaflavin 3,3'-digallate, each as a separate compound, pharmaceutical compositions of the above compounds, diet supplement compositions of the above compounds and methods for using the above compounds to treat or prevent various diseases.

2. BACKGROUND OF THE INVENTION

Tea, which is the most widely consumed beverage in the world other than water, is produced from the leaves of *Camellia Sinensis* and contain significant amounts of flavanoid compounds. Theaflavins, which comprise a mixture of theaflavin, theaflavin-3-gallate, theaflavin-3'-gallate and theaflavin-3,3'-digallate, as depicted in FIG. 1, are typically formed via polymerization of green tea polyphenols (i.e., flavanoids) during fermentation of green tea to black tea. Typically, the concentration of theaflavins in black tea is between about 0.4% to about 1.8% by weight with the concentration of theaflavins in green tea usually being far less.

Theaflavins are responsible for the characteristic color (i.e., brightness) and flavor (i.e., briskness) of black tea. Flavanoids are effective anti-oxidants (Leung et al., *J Nutr* 2001, 131(9):2248-51; Sarkar et al., *Biochem Biophys Res Commun* 2001, 284(1):173-8; Yoshino et al., *Biol. Pharm Bull.* 1994, 17(1) 146-149) and may be efficacious against various diseases such as cancer, cardiovascular and cerebrovascular diseases, diabetes, etc. Further, flavanoids may possess significant anti-inflammatory antimicrobial and antiviral activity.

However, a significant problem in using theaflavins to treat or prevent various diseases is isolating theaflavins, either as a mixture or as individual compounds, in sufficient quantities, from naturally occurring sources using an economical procedure. Thus, what is needed are methods for isolating theaflavins, either as a mixture or as individual compounds, in sufficient quantities in a cost effective manner so that theaflavins, either as a mixture or as individual compounds, may be used to treat or prevent various diseases.

3. SUMMARY OF THE INVENTION

The present invention satisfies these and other needs by providing methods of making a mixture of theaflavin, theaflavin-3-gallate, theaflavin-3'-gallate and theaflavin 3,3'-digallate and methods of making theaflavin, theaflavin-3-gallate, theaflavin-3'-gallate and theaflavin 3,3'-digallate, each as a separate compound and methods of using either the mixture of theaflavins or individual theaflavins to treat or prevent various diseases. Importantly, the methods above are efficiently carried out on large scale at minimal cost.

In one aspect, the current invention provides a method of making a mixture of theaflavin, theaflavin-3-gallate, theaflavin-3'-gallate and theaflavin 3,3'-digallate. Green tea leaves are contacted with an aqueous buffer to form a reaction mixture. The reaction mixture is then contacted with oxygen to begin fermentation and is fermented for a time sufficient to form the mixture of theaflavin, theaflavin-3-gallate, theaflavin-3'-gallate and theaflavin 3,3'-digallate. Fermentation is then terminated and the reaction mixture is separated from the mixture of theaflavin, theaflavin-3-gallate, theaflavin-3'-gallate and theaflavin 3,3' digallate.

In another aspect, the present invention provides pharmaceutical compositions comprising the mixture of theaflavin, theaflavin-3-gallate, theaflavin-3'-gallate and theaflavin 3,3'-digallate or a pharmaceutically available salt, hydrate or solvate thereof. The pharmaceutical compositions generally comprise the mixture of theaflavin, theaflavin-3-gallate, theaflavin-3'-gallate and theaflavin 3,3'-digallate or a pharmaceutically available salt, hydrate or solvate thereof and a suitable excipient, carrier or diluent. The composition may be formulated for veterinary uses or for use in humans.

In still another aspect, the present invention provides diet supplement compositions comprising the mixture of theaflavin, theaflavin-3-gallate, theaflavin-3'-gallate and theaflavin-3,3'-digallate. The diet supplement compositions generally comprise the mixture of theaflavin, theaflavin-3-gallate, theaflavin-3'-gallate and theaflavin-3,3'-digallate or a pharmaceutically available salt, hydrate or solvate thereof and a suitable diet supplement vehicle.

In still another aspect, the present invention provides methods of treating or preventing various diseases, which include, but are not limited to, hyperlipidemia, coronary heart disease, apoplexy, atherosclerotic cardiovascular disease, diabetes, leucopenia, cerebral infarction and dementia or physical disorder. The methods may comprise administering to a patient in need of such treatment or prevention a therapeutically effective amount of the mixture of theaflavin, theaflavin-3-gallate, theaflavin-3'-gallate and theaflavin-3,3'-digallate or a pharmaceutically available salt, hydrate or solvate thereof. Alternatively, the methods may comprise administering to a patient in need of such treatment or prevention a therapeutically effective amount of the above pharmaceutical composition of the mixture of theaflavins.

In still another aspect, the current invention provides a method of making theaflavin, theaflavin-3-gallate, theaflavin-3'-gallate or theaflavin-3,3'-digallate, each as a separate compound. Tea polyphenols are contacted with an aqueous buffer and polyphenol oxidase to form a reaction mixture. The reaction mixture is then contacted with oxygen to begin fermentation and is fermented for a time sufficient to form a mixture of theaflavin, theaflavin-3-gallate, theaflavin-3'-gallate and theaflavin-3,3'-digallate. Fermentation is then terminated and the reaction mixture is separated to provide theaflavin, theaflavin-3-gallate, theaflavin-3'-gallate and theaflavin-3,3' digallate, each as a separate compound.

In still another aspect, the present invention provides pharmaceutical compositions comprising theaflavin, theaflavin-3-gallate, theaflavin-3'-gallate or theaflavin-3,3'-digallate. The pharmaceutical compositions generally comprise theaflavin, theaflavin-3-gallate, theaflavin-3'-gallate, theaflavin-3,3'-digallate or pharmaceutically available salts, hydrates or solvates thereof and a suitable excipient, carrier or diluent. The pharmaceutical composition may be formulated for veterinary uses or for use in humans.

In still another aspect, the present invention provides diet supplement compositions comprising theaflavin, theaflavin-3-gallate, theaflavin-3'-gallate or theaflavin-3,3'-digallate. The diet supplement compositions generally comprise theaflavin, theaflavin-3-gallate, theaflavin-3'-gallate, theaflavin-3,3'-digallate or pharmaceutically available salts, hydrates or solvates thereof and a suitable diet supplement vehicle.

In still another aspect, the present invention provides methods of treating or preventing various therapeutic indications, which include, but are not limited to, hyperlipidemia, coronary heart disease, apoplexy, atherosclerotic cardiovascular disease, diabetes, leucopenia, cerebral infarction and dementia or physical disorder. The methods may comprise administering to a patient in need of such treatment or prevention a therapeutically effective amount of theaflavin, theaflavin-3-gallate, theaflavin-3'-gallate, theaflavin-3,3'-digallate or pharmaceutically available salts, hydrates or solvates thereof. Alternatively, the methods may comprise administering to a patient in need of such treatment or prevention a therapeutically effective amount of the above pharmaceutical compositions of theaflavin, theaflavin-3-gallate, theaflavin-3'-gallate or theaflavin-3,3'-digallate.

3. BRIEF DESCRIPTION OF THE DRAWINGS

Figure 2:
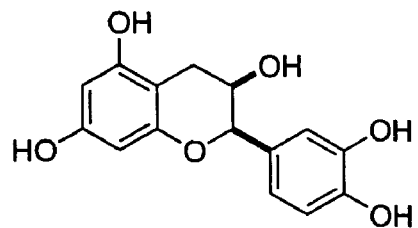
Figure 2:
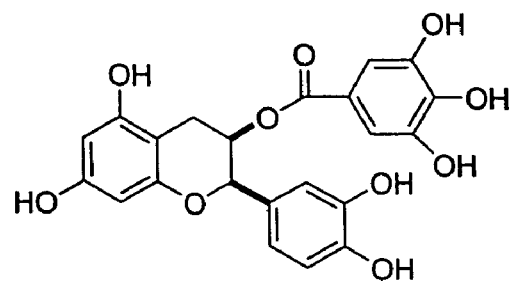
Figure 2:
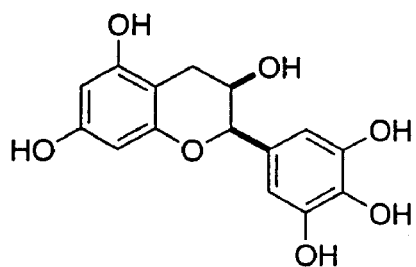
Figure 2:
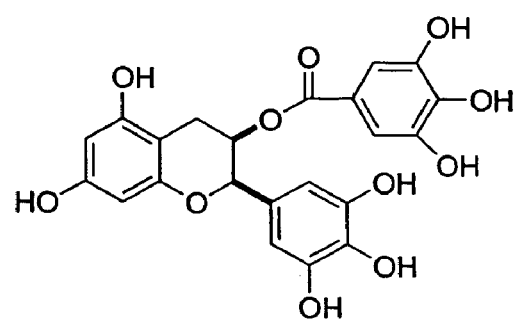

FIG. 1 illustrates the chemical structure of theaflavin, theaflavin-3-gallate, theaflavin-3'-gallate and theaflavin-3,3'-digallate; and FIG. 2 illustrates the chemical structure of epicatechin, epicatechin gallate, epigallocatechin and epigallocatechin.

4. DETAILED DESCRIPTION OF THE INVENTION

4.1 Definitions

"Buffer" refers to a substance which binds reversibly with hydrogen ion and consequently resists change in pH upon addition of acid or base. Examples of buffers include, but are not limited to, proteins, bicarbonates, carbonates, carboxylates (e.g., acetate, propionate, etc.), sulfonates, phosphates (e.g., sodium phosphate), citrates, borates, amino acids (e.g., glycine, alanine, etc.) and amines (e.g., methylamine, ethylamine, Tris, etc.).

"Compounds of the invention" refers to any mixture of the theaflavins as well as theaflavin, theaflavin-3-gallate, theaflavin-3'-gallate and theaflavin 3,3'-digallate individually. The compounds of the invention may be identified either by their chemical structure and/or chemical name. When the chemical structure and chemical name conflict, the chemical structure is determinative of the identity of the compound. The compounds of the invention may also exist in several tautomeric forms including the enol form, the keto form and mixtures thereof. Accordingly, the chemical structures depicted herein encompass all possible tautomeric forms of the illustrated compounds. The compounds of the invention may also include isotopically labeled compounds where one or more atoms have an atomic mass different from the atomic mass conventionally found in nature. Examples of isotopes that may be incorporated into the compounds of the invention include, but are not limited to, $^2$H, $^3$H, $^{13}$C, $^{14}$C, $^{18}$O and $^{17}$O. Compounds of the invention may exist in unsolvated forms as well as solvated forms, including hydrated forms. In general, hydrated and solvated forms are within the scope of the present invention. Certain compounds of the present invention may exist in multiple crystalline or amorphous forms. In general, all physical forms are equivalent for the uses contemplated by the present invention and are intended to be within the scope of the present invention.

"Green tea leaves" refers to leaves of the evergreen species *Camellia Sinensis* which have been withered, heated (e.g., pan fried or steamed) to prevent the oxidation (i.e., fermentation) process and then naturally dried.

"Pharmaceutically acceptable salt" refers to a salt of a compound of the invention, which is pharmaceutically acceptable and possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by an ammonium ion, a metal ion, e.g., an alkali metal ion (e.g., sodium or potassium), an alkaline earth ion (e.g., calcium or magnesium), or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galactunoric acids and the like (see, e.g., Berge et al., 1977, *J. Pharm. Sci.* 66:1-19).

"Pharmaceutically acceptable vehicle" refers to a diluent, adjuvant, excipient or carrier with which a compound of the invention is administered.

"Patient" includes humans and other mammals.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Theaflavins" refers to those compounds that are formed by the oxidative condensation of a catechin quinone (e.g., epicatechin) and a gallocatechin quinone (e.g., epigallocatchin), a reaction which may be catalyzed by the enzyme polyphenol oxidase. Theaflavins include theaflavin, theaflavin-3-gallate, theaflavin-3'-gallate and theaflavin 3,3'-digallate. Theaflavins are soluble in hot water, ethyl acetate, butanol and methanol, etc. and are typically sensitive to oxidation in basic solution.

"Tea polyphenols" refers to a mixture of polyphenols extracted from green tea leaves with catechins comprising about 90% of the mixture. Tea polyphenols are available from commercial sources (e.g., Wuzhou International Co., LTD., Ningbo Free Trade Zone, Ningbo, China). Catechins include gallocatechin, epicatechin ("EC"), epigallocatechin ("EGC") epicatechin gallate ("EGC"), epigallocatechin gallate ("EGCG"). Typically EGCG comprises about 50% to about 60% of the catechin content.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating or preventing a disease, is sufficient to effect such treatment or prevention of the disease. The "therapeutically effective amount" will vary depending on the compound, the disease and its severity and the age, weight, etc., of the patient to be treated.

4.2 Method of Making Theaflavin Mixtures and Individual Theaflavins

In one aspect, the current invention provides a method of making a mixture of theaflavin, theaflavin-3-gallate, theaflavin-3'-gallate and theaflavin-3,3'-digallate. First, green tea leaves, are contacted with an aqueous buffer to form a reaction mixture. Green tea leaves may be purchased from commercial sources (e.g., Far Tea Leaves, Berkeley, Calif.; SOTA Instant Japanese Green Tea, Reno, Nev.; FML Tea Trading Co., Ltd., Xiamen, China) and may be used as provided by the supplier or maybe shredded prior to contacting with buffer.

Preferably, the aqueous buffer has a pH of between about 5.0 and about 7.0 (more preferably, between about 6.3 and about 6.5). The molar amount of buffer should be enough to buffer the aqueous solution and may be readily approximated by the skilled artisan. In one embodiment, the buffer is between about 0.1 M and about 0.3 M. The buffer may be selected from any buffering agent which can be adjusted to the desired pH of the reaction mixture. Methods for selecting an appropriate buffering agent are well know to the skilled artisan. Preferred buffers include phosphate. In one embodiment, the buffering agent is 0.15 M phosphate at pH 6.4. In another embodiment, the ratio of green tea leaves to aqueous buffer is between about 1:0.5 and about 1:20 on a kilogram to liter basis.

In some cases, the green tea leaves may contain enough residual polyphenol oxidase to convert catechins to theaflavins. In other situations, polyphenol oxidase (Worthington Biochemical Corporation, Lakewood, N.J.) may be added to the reaction mixture to assist in formation of theaflavins from catechins. Typically, the ratio of polyphenol oxidase to green tea leaves may vary between about 0.1:1 and about 2:1 (w/w).

The reaction mixture is then contacted with oxygen to initiate fermentation. Typically the reaction is agitated and preferably, is stirred. The amount of oxygen in the reaction mixture may vary between about 20% and about 25% (w/v). The appropriate oxygen flow rate through the reaction mixture will vary with the reaction volume and may be readily determined by the skilled artisan. In one embodiment, the amount of oxygen in the reaction mixture is about 22% (w/v).

The temperature of the reaction mixture may vary between about 15° C. and about 80° C. In one embodiment, the temperature is about 30° C. In another embodiment, the amount of oxygen in the reaction mixture is about 22% (w/v), the flow rate of oxygen through the reaction mixture is about 20 L/sec, the volume of the reaction mixture is between about 1000 L and about 1200 L, the temperature is about 30° C. and the reaction mixture is stirred.

The reaction mixture is then fermented to form the mixture of theaflavin, theaflavin-3-gallate, theaflavin-3'-gallate and theaflavin-3,3'-digallate. Typically the reaction mixture is fermented between about 0.5 hours and about 1.5 hours. In one embodiment, the reaction mixture is fermented for about 1 hour. It should be noted that the temperature and oxygen concentration of the reaction mixture remain roughly constant during fermentation. Preferably, the reaction mixture is agitated during fermentation, more preferably, the reaction mixture is stirred during fermentation.

Finally, the reaction mixture is separated from the mixture of theaflavin, theaflavin-3-gallate, theaflavin-3'-gallate and theaflavin-3,3'-digallate. Preferably, any solids in the reaction mixture are removed. The reaction mixture may be filtered to remove solids. More preferably, the reaction mixture is centrifuged to remove solids. Even more preferably, the reaction mixture is both centrifuged and filtered to remove solids.

The filtered reaction mixture is then contacted with organic solvent, which terminates fermentation. The organic solvent should dissolve appreciable quantities of theaflavins (i.e., theaflavins should be more than sparingly soluble in the selected solvent) and be at least partially immiscible with aqueous solutions (i.e., the aqueous phase and the organic phase should form two phases after mixing). The organic solvent may be selected without undue experimentation by those of skill in the art given the above criteria. In a preferred embodiment, the organic solvent is ethyl acetate. It should be noted that mixtures of organic solvents can be used in the extractive method, provided the solvent mixture satisfies the above criteria.

Calculating the volume of organic solvent needed for extraction of theaflavins from aqueous solution are well within the capability of the skilled artisan. Preferably, the volume of organic solvent used to extract theaflavins from aqueous solution is between about ⅓ of the volume of the aqueous solution and about three times the volume of the aqueous solution. More preferably, the volume of organic solvent used to extract theaflavins from aqueous solution is about equal to the volume of the aqueous solution.

The aqueous solution may be contacted with as many portions of organic solvent necessary to extract substantially all of the theaflavins into the organic phase. The number of portions of organic solvent necessary to completely extract theaflavins from aqueous solution may be readily determined by one of skill in the art without undue experimentation.

Generally, contacting organic solvent and aqueous solution in a separatory funnel is sufficient to extract theaflavins into organic solvent from aqueous solution. However, in some situations, the organic solvent and aqueous solution may be contacted by other methods well known to the skilled artisan such as magnetic stirring, mechanical stirring, sonication, etc.

The organic solvent containing the theaflavins is then contacted with dilute aqueous base. Preferably, the base is dilute hydroxide, carbonate or bicarbonate. In one embodiment, the dilute aqueous base is 5% $NaHCO_3$, which is contacted with organic solvent in a separatory funnel. While not wishing to bound by theory, contacting the organic solvent with dilute base presumably removes base soluble impurities from the mixture of theaflavins. The solvent is next separated from the dilute aqueous base solution, preferably, by using a separatory funnel.

In one embodiment, the concentration of the mixture of theaflavins in the reaction mixture after extractive workup comprises between about 5% and about 90% of the total mass of non-volatile material. In another embodiment, the concentration of the mixture of theaflavins in the reaction mixture after extractive workup comprises between about 10% and about 80% of the total mass of non-volatile material. In another embodiment, the concentration of the mixture of theaflavins in the reaction mixture after extractive workup comprises between about 20% and about 70% of the total mass of non-volatile material.

The separated organic solvent is then contacted with a chromatographic media to provide the mixture of theaflavin, theaflavin-3-gallate, theaflavin-3'-gallate and theaflavin-3,3'-digallate. Preferably, the organic solution is concentrated before contacting with the chromatographic media. The chromatographic media may be any chromatography support known to those of skill in the art. In one embodiment, the chromatographic media is silica gel. Preferably, the organic solvent containing the mixture of theaflavins is loaded onto chromatographic media, which has been packed in a column and eluted with a second organic solvent to provide the mixture of theaflavin, theaflavin-3-gallate, theaflavin-3'-gallate and theaflavin-3,3'-digallate. In one embodiment, the organic solvent containing the mixture of theaflavins is loaded onto a silica gel column and is eluted with 40% ethyl acetate in hexanes. In some situations, batch use of chromatographic media may be preferred. Selection of the type and amount of chromatographic media, choice of eluting solvent, length of column, etc. is within the ambit of those of skill in the art.

In one embodiment, the mixture of theaflavin, theaflavin-3-gallate, theaflavin-3'-gallate and theaflavin-3,3'-digallate is substantially pure (i.e., free of other material) after elution from the chromatographic media. Preferably, the mixture of theaflavin, theaflavin-3-gallate, theaflavin-3'-gallate and theaflavin-3,3'-digallate is greater than 95% pure, more preferably, greater than 97% pure and most preferably, greater than 99% pure as determined by routine analytical methods well known to those of skill in the art.

The proportion of the individual theaflavins in the mixture of theaflavins will reflect the proportion of individual theaflavins in green tea leaves and will, accordingly, vary with source of green tea leaves. In one embodiment, the mixture of theaflavins is comprised of between about 40% and about 50% theaflavin, between about 15% and about 25% of theaflavin-3-gallate, between about 10% and about 14% theaflavin-3'-gallate and between about 15% and about 25% of theaflavin-3,3'-digallate. In another embodiment, the mixture of theaflavins is comprised of about 47% theaflavin, about 19% of theaflavin-3-gallate, about 14% theaflavin-3'-gallate and about 20% of theaflavin-3,3'-digallate.

In a second aspect, the current invention provides a method of making theaflavin, theaflavin-3-gallate, theaflavin-3'-gallate and theaflavin-3,3'-digallate, each as a separate compound. First, tea polyphenols, are contacted with an aqueous buffer to form a reaction mixture. Tea polyphenols may be purchased from commercial sources (Yuan Xiang Biopharm Company, Ltd., Shanghai, China) and may be used as provided by the supplier. Polyphenol oxidase (Worthington Biochemical Corporation, Lakewood, N.J.) is added to the reaction mixture. Typically, the ratio of polyphenol oxidase to tea polyphenols may vary between about 0.5:1 and about 1:1 on a w/w basis. The remainder of the method may be performed as described above for forming the mixture of theaflavin, theaflavin-3-gallate, theaflavin-3'-gallate and theaflavin-3,3'-digallate from green tea leaves except for the final purification on a chromatographic media. Preferably, the mixture of theaflavins is divided into a number of different portions, which are then individually applied to columns of chromatographic media to provide theaflavin, theaflavin-3-gallate, theaflavin-3'-gallate and theaflavin-3,3'-digallate, each as a single compound rather than as a mixture of compounds. Selection of the parameters needed to resolve the mixture of theaflavins into theaflavin, theaflavin-3-gallate, theaflavin-3'-gallate and theaflavin-3,3'-digallate each as a single compound (i.e., number of portions, selection of type and amount of chromatographic media, choice of eluting solvent, length of column, etc.) is well within the ambit of those of skill in the art.

4.3 Therapeutic Uses

The compounds of the invention may be used to treat a variety of diseases and disorders, which include but are not limited to, hyperlipidemia, coronary heart disease, apoplexy, arthesclerotic cardiovascular diseases, AIDS, diabetes, oxidated-low density lipoprotein level, von Willebrand's disease, leukopenia, cerebral infarction, dementia and physical disorder, fatty liver. Description of the symptoms of these diseases and disorders may be found, for example, in the Merck Manual, sixteenth edition. In a preferred embodiment, a compound of the invention and/or a pharmaceutical composition thereof is administered to a patient, preferably a human, suffering from hyperlipidemia.

Further, in certain embodiments, compounds of the invention and/or pharmaceutical compositions thereof are administered to a patient, preferably a human, as a preventative measure against the above diseases or conditions. Thus, the compounds of the invention and/or pharmaceutical compositions thereof may be administered as a preventative measure to a patient having a predisposition for any of the above diseases or disorders. Accordingly, the compounds of the invention and/or pharmaceutical compositions thereof may be used for the treating or preventing one disease or disorder and concurrently treating or preventing another (e.g., preventing hyperlipidemia while treating a cerebral infarction).

The suitability of the compounds of the invention and/or pharmaceutical compositions thereof in treating or preventing the various diseases or disorders listed above may be determined by methods described in the art. Accordingly, it is well within the capability of those of skill in the art to assay and use the compounds of the invention and/or pharmaceutical compositions thereof to treat or prevent the above diseases or disorders.

4.4 Therapeutic/Prophylactic Administration

The compounds of the invention and/or pharmaceutical compositions thereof may be advantageously used in human and veterinary medicine. As previously described in Section 4.3 above, compounds of the invention and/or pharmaceutical compositions thereof are useful for the treatment or prevention of various diseases or disorders listed above.

When used to treat or prevent the above diseases or disorders, compounds of the invention and/or pharmaceutical compositions thereof may be administered or applied singly, or in combination with other agents. The compounds of the invention and/or pharmaceutical compositions thereof may also be administered or applied singly, in combination with other pharmaceutically active agents including other compounds of the invention and/or pharmaceutical compositions thereof.

The current invention provides methods of treatment and prophylaxis by administration to a patient of a therapeutically effective amount of a compound of the invention and/or pharmaceutical composition thereof. The patient is preferably a mammal and most preferably, is a human.

The compounds of the invention and/or pharmaceutical compositions thereof are preferably administered orally, which results in the release of the compounds of the invention and/or pharmaceutical compositions thereof into the bloodstream. The compounds of the invention and/or pharmaceutical compositions thereof can be delivered via oral sustained release systems. In one embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropyl methylcellulose). Other preferred cellulose ethers have been described (Alderman, *Int. J. Pharm. Tech. & Prod. Mfr.* 1984, 5(3) 1-9). Factors affecting drug release are well known to the skilled artisan and have been described in the art (Bamba et al., *Int. J. Pharm.* 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still another embodiment, osmotic delivery systems are used for oral sustained release administration (Verma et al., *Drug Dev. Ind. Pharm.*, 2000, 26:695-708). In still another embodiment, OROS™ osmotic devices are used for oral sustained release delivery devices (Theeuwes et al., U.S. Pat. No. 3,845,770; Theeuwes et al., U.S. Pat. No. 3,916,899).

In one embodiment, the compounds of the invention are encapsulated for oral administration. Preferably, encapsulation protects the compounds of the invention from light and/or oxygen degradation. The capsule preferably, is comprised of a shell and a fill material, where either the shell or fill material contains an radiation blocker and/or an anti-oxidant.

The shell material is comprised of a gelling agent, water and optionally a plasticizer. Accordingly, the shell material may form either a hard gel or a soft gel. The gelling agent may be, but is not limited to, gelatin, modified starch, carrageenan, gellan, mannan gum, amylose, xanthan, alginates, agar, guar, gum arabic, pectin, cyclodextrin or combination thereof. The shell may optionally include an emulsifier, thickener, preservative, flavoring, sweetener, colorant, radiation blocker, opacifying agent, anti-oxidant, masticatory substance, etc.

Gelatin, as is well known in the art, is manufactured by the hydrolysis of animal by-products such as bones, skin, and connective tissue which contain collagen. Bovine animals and pigs are the primary sources of gelatin Modified starches, include, for example, non-retrograding starches derived by chemical modification of starch from any plant source such as corn, waxy maize, potato, wheat, rice, tapioca, sorghum, etc. Useful modified starches are ether and ester derivatives of starch including, for example, hydroxypropyl, hydroxyethyl, succinate, and octenyl succinate starch derivatives. Other modified starches which may be used include the thermally converted, fluidity or thin boiling type products derived from the above chemically modified starches. These materials may be of lower molecular weight, prepared by heating the modified starch, subjecting the starch to hydrolytic acid and/or heat treatment, etc.

Carrageenan is a natural sulfated polysaccharide hydrocolloid derived from seaweed, and is a mixture of galactose and 3-6-anhydrogalactose copolymers. A number of different carrageenan types exist (e.g., kappa, iota, lambda, etc.) and it is anticipated that any of these may be used in the present invention.

Gellan gum is an extracellular polysaccharide obtained by aerobic fermentation of the microorganism, *Pseudomonas elodea*. Various forms of gellum gum including, but not limited to, native, deacetylated, deacylated clarified, partially deacetylated, partially deacylated clarified may be sued in the present invention.

Mannam gum include the galactomannan gums, the glucomannan gums and mixtures thereof. Accordingly, mannam gum includes, but is not limited to, locust bean gum, konjac gum, tara gum and cassia gum.

In some embodiments, a gelling salt may be used in the present invention. Accordingly, a calcium salt, a magnesium salt, a barium salt, a sodium salt or a potassium salt of an appropriate inorganic or organic acid may be used to form the shell of a capsule of the present invention.

Plasticizers are preferably, polyols, such as, for example, glycerin, sorbitol, an alkylene glycol, maltitol, lactitol, xylitol, corn syrup solids, etc. and combinations thereof. In one embodiment, the plasticizer is a combination of glycerin and sorbitol.

In another embodiment, the capsule shell comprises between about 10% and 90% gelatin, and between about 5% and about 40% water. In another embodiment, the capsule shell comprises between about 10% and 90% gelatin, between about 1% and about 30% plasticizer and between about 5% and about 40% water. In still another embodiment, the capsule shell comprises between about 25 to about 45% gelatin, between about 1% and about 30% plasticizer and between about 5% and about 40% water. In still another embodiment, the capsule shell comprises between about 25 to about 45% gelatin, between about 1% and about 30% plasticizer, between about 1 and 5% radiation blocker and between about 1% and about 5% colorant and between about 5% and about 40% water.

The capsule shell of the present invention encloses a preselected quantity of fill material. Preferably, the enclosed fill material will contain a therapeutically effective amount of a mixture of theaflavins. The fill material may be a liquid, a semi-solid, a solid and gel.

The fill material may include a pharmaceutically acceptable vehicle, which may be prepared by a number of diverse methods which are known to those of skill in the art. The pharmaceutically acceptable vehicle must be compatible with the capsule shell and preferably, does not degrade the capsule shell during a period of typical storage. Solutions to the above problem are well known to the skilled artisan.

Suitable liquid pharmaceutically acceptable vehicles for the fill material include, but are not limited to, neutral oil, mineral oil, water, alcohol, polyalkylene glycol, vegetable oil and fructose syrup. Preferably, the liquid pharmaceutically acceptable vehicle is a vegetable oil, more preferably, a corn oil, peanut oil, safflower oil, sunflower oil and soybean oil and most preferably soybean oil. The liquid pharmaceutically acceptable vehicle may include an emulsifier, thickener, preservative, flavoring, sweetener, colorant, radiation blocker, opacifying agent, anti-oxidant, masticatory substance, etc.

The present capsules may also include a solid fill material. Useful solid fill materials include, but are not limited to, tablets or pellets comprising the mixture of theaflavins, which may be further coated with gelatin, sugar, etc. (Glassman, U.S. Pat. No. 3,228,789). The tablets or pellets may contain co-solvents, buffers, emulsifiers, thickeners, preservatives, sweeteners, flavorings, colorants, radiation blockers, antioxidants, opacifying agent, masticatory substances, etc.

The present capsules may also include a semi-solid fill material. The mixture of theaflavins may, for example, be dispersed in a substantially water-free carrier mixture comprising one or more polyalkylene glycols, preferably, comprising a mixture of liquid polyalkylene glycol and waxy polyalkylene glycol and in minor amount a $C_2$-$C_4$ diol or triol (Shah et al., U.S. Pat. No. 4,935,243). A flavoring, preservative, sweetener, colorant, radiation blocker, co-solvent, buffer, emulsifier, thickener, anti-oxidant, opacifying agent, masticatory substance, etc., may be added to the semi-solid fill material.

The present capsules may also enclose a gel fill comprising a gelled polymeric matrix, which may be generated by gelling a liquid fill followed by encapsulation (Cohen et al, U.S. Pat. No. 4,708,834). The gelled fill may comprise a solution or dispersion of an active ingredient in a polysaccharide gum and may also optionally, include co-solvents, preservative, buffers, emulsifiers, thickeners, sweeteners, flavorings, colorant, radiation blocker, opacifying agent, anti-oxidant, masticatory substance, etc.

Masticatory substances, for example, include, but are not limited to, Chicle, Chiquibul, Crown gum, Gutta hang kang, Massaranduba balata, Massaranduba chocolate, Nispero, Leche caspi, Pendare, Perillo, Leche de vac, Niger gutta, Tunu, Chite and Natural rubber. Flavorings include, but are not limited to, cherry syrup, citric acid, dextrose, essential oil, vanillin, cinnamon oil, orange oil, spearmint oil, strawberry oil, nutmeg oil. A preferred stiffener is beeswax while a preferred emulsifier is lecithin. Other stiffeners and emulsifiers which may be useful in the present invention are known to the skilled artisan. Preferred anti-oxidants include ascorbic acid and vitamin E.

In one embodiment, the fill material comprises between about 1% and about 20% mixture of theaflavins, between about 1% and about 5% anti-oxidant, between about 5% and about 90% pharmaceutically acceptable carrier, between about 1% and about 20% emulsifier; and between about 1% to about 20% stiffening agent.

4.5 Pharmaceutical Compositions

The present pharmaceutical compositions typically contain a therapeutically effective amount of a compound of the invention, preferably in purified form, together with a suitable amount of a pharmaceutically acceptable vehicle, so as to provide the form for proper administration to a patient. The compounds of the invention may be present at a level of between about 5% and about 50% (w/w), preferably, about 11% in the pharmaceutical composition. Total amount of the compound of the invention per dose may be between about 70 mg and about 210 mg.

When administered to a patient, the compounds of the invention and pharmaceutically acceptable vehicle are preferably sterile. Water, saline solutions and aqueous dextrose and glycerol solutions may be employed as liquid vehicles. Other suitable pharmaceutical vehicles include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emu 1 sifying agents or pH buffering agents. In addition, auxiliary, stabilizing, thickening, lubricating and coloring agents may be used. A general discussion of the preparation of pharmaceutical compositions may be found in Remington, "The Science and Practice of Pharmacy," 19$^{th}$ Edition.

Pharmaceutical compositions comprising a compound of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the invention into preparations which can be used pharmaceutically.

The present pharmaceutical compositions can take the form of solutions, suspensions, emulsion, tablets, pills, pellets, capsules, capsules containing liquids, powders, sustained-release formulations, emulsions or any other form suitable for oral use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington, "The Science and Practice of Pharmacy," 19$^{th}$ Edition, 1995). Orally administered pharmaceutical compositions may contain one or more optional agents, for example, sweetening agents such as fructose, aspartame or saccharin; flavoring agents such as peppermint, oil of wintergreen, or cherry coloring agents and preserving agents, to provide a pharmaceutically palatable preparation. Moreover, when in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM), etc. Additionally, flavoring agents, preservatives, coloring agents, bile salts, acylcamitines and the like may be added. For buccal administration, the pharmaceutical compositions may take the form of tablets, lozenges, etc. formulated in conventional manner.

When a compound of the invention is acidic or basic, it may be included in any of the above-described formulations as the free acid or free base, a pharmaceutically acceptable salt, a solvate or hydrate. Pharmaceutically acceptable salts substantially retain the activity of the free acid or base, may be prepared by reaction with bases or acids and tend to be more soluble in aqueous and other protic solvents than the corresponding free acid or base form.

4.6 Therapeutic Doses

A compound of the invention and/or pharmaceutical composition thereof, will generally be used in an amount effective to achieve the intended purpose. For use to treat or prevent the above diseases or disorders the compounds of the invention and/or pharmaceutical compositions thereof, are administered or applied in a therapeutically effective amount.

The amount of a compound of the invention and/or pharmaceutical composition thereof that will be effective in the treatment of a particular disorder or condition disclosed herein will depend on the nature of the disorder or condition, and can be determined by standard clinical techniques known in the art and by doctors skilled in treating or preventing a particular disease or disorder. In addition, in vitro or in vivo assays may optionally be employed to help identify optimal dosage ranges. The amount of a compound of the invention and/or pharmaceutical composition thereof administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In one embodiment, the compounds of the invention are delivered by oral sustained release administration. Preferably, in this embodiment, the compounds of the invention are administered twice per day (more preferably, once per day). Dosing may be repeated intermittently, may be provided alone or in combination with other drugs and may continue as long as required for effective treatment of the disease state or disorder.

Suitable dosage ranges for oral administration are dependent on the nature of the compounds of the invention administered (e.g., whether the theaflavins are administered together or whether theaflavin, theaflavin-3-gallate, theaflavin-3'-gallate or theaflavin-3,3'-digallate are administered, each as a separate compound) but are generally about 0.001 mg to about 200 mg of a compound of the invention per kilogram body weight. In one embodiment, the dosage range is between about 0.1 mg/kg to about 5 mg/kg. Dosage ranges may be readily determined by methods known to the artisan of ordinary skill. Effective doses may be extrapolated from dose-response curves derived from in vitro or animal model test systems. Such animal models and systems are well-known in the art.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred. The compounds of the invention may also be demonstrated to be effective and safe using animal model systems.

Preferably, a therapeutically effective dose of a compound of the invention and/or pharmaceutical composition thereof described herein will provide therapeutic benefit without causing substantial toxicity. Toxicity of compounds of the invention and/or pharmaceutical compositions thereof may be determined using standard pharmaceutical procedures and may be readily ascertained by the skilled artisan. The dose ratio between toxic and therapeutic effect is the therapeutic index. A compound of the invention and/or pharmaceutical composition thereof will preferably exhibit particularly high therapeutic indices in treating disease and disorders. The dosage of a compound of the invention and/or pharmaceutical composition thereof described herein will preferably be within a range of circulating concentrations that include an effective dose with little or no toxicity.

4.7 Combination Therapy

In certain embodiments of the present invention, the compounds of the invention and/or pharmaceutical compositions thereof can be used in combination therapy with at least one other therapeutic agent. The compound of the invention and/or pharmaceutical composition thereof and the therapeutic agent can act additively or, more preferably, synergistically. In a preferred embodiment, a compound of the invention and/or a pharmaceutical composition thereof is administered concurrently with the administration of another therapeutic agent. In another embodiment, a compound of the invention and/or pharmaceutical composition thereof is administered prior or subsequent to administration of another therapeutic agent.

In particular, in one preferred embodiment, the compounds of the invention and/or pharmaceutical compositions thereof can be used in combination therapy with other agents used to treat or prevent hyperlipidemia, coronary heart disease, apoplexy, arthesclerotic cardiovascular diseases, AIDS, diabetes, oxidated-low density lipoprotein level, von Willebrand's disease, leukopenia, cerebral infarction, dementia and physical disorder and fatty liver.

4.8 Diet Supplement Compositions

The present diet supplement compositions typically contain one or more compounds of the invention, preferably in purified form, together with a suitable amount of a diet supplement vehicle, so as to provide the form for proper administration to a user.

5. EXAMPLES

The invention is further defined by reference to the following examples, which describe in detail, preparation of compounds of the invention and methods for assaying for biological activity. It will be apparent to those skilled in the art that many modifications, both to materials and methods, may be practiced without departing from the scope of the invention.

Example 1

Preparation and Isolation of the Mixture of Theaflavin, Theaflavin-3-gallate, Theaflavin-3'-gallate and Theaflavin-3,3' digallate Green tea leaves (100 kg) obtained from FML Tea Trading Co., Ltd., Xiamen, China and 0.15 M phosphate buffer (1000 L, pH 6.4) was added to a slurry fermenter maintained at 30° C. Oxygen was added to the fermenter at a flow rate of 20 L/sec until the total oxygen concentration was 22%, to initiate fermentation. The reaction mixture was stirred and fermented for about 1 hour under a 22% oxygen atmosphere.

The reaction mixture was centrifuged and the supernatant decanted. The supernatant was filtered to remove solids. About 1000 L of ethyl acetate was added to the aqueous filtrate, which terminated fermentation and the layers were separated. The organic layer was washed three times with 1000 L of 5% $NaHCO_3$ and ethyl acetate was removed in vacuo. Then, the residue was dissolved in a small portion of 40% ethyl acetate/hexanes, loaded onto a column, which contained 150 kg of silica gel and eluted with 40% ethyl acetate/hexanes to provide a mixture of theaflavin, theaflavin-3-gallate, theaflavin-3'-gallate and theaflavin-3,3' digallate (typically, between about 50 kg to 60 kg) in 99.3% purity as determined by reverse phase High Pressure Reverse Phase Chromatography (HPLC). The mixture of theaflavins comprised 46.8% theaflavin, 18.5% theaflavin-3-gallate, 13.7% theaflavin-3'-gallate and 20.3% theaflavin-3,3' digallate as determined by HPLC-MS.

Example 2

Preparation and Isolation of Theaflavin, Theaflavin-3-gallate, Theaflavin-3'-gallate and Theaflavin-3,3' digallate, Each as a Separate Compound Tea polyphenol (100 kg), which contains 98.6%, catechins (45.6% epigallocatechin gallate), (Yuan Xiang Biopharm Company, Ltd., Shanghai, China), 1000 L of 0.15 M phosphate buffer (pH 6.4) and 10 kg of polyphenol oxidase was added to a slurry fermenter at 25° C. with stirring. Oxygen at a flow rate of 20 L/sec was added to the fermenter until the total oxygen concentration was 22%, to initiate fermentation. The reaction mixture was stirred and fermented for about 40 minutes under a 22% oxygen atmosphere.

The reaction mixture was centrifuged and the supernatant decanted. The supernatant was filtered to remove solids. About 1000 L of ethyl acetate was added to the aqueous filtrate, which terminated fermentation and the layers were separated. The organic layer was washed three times with 1000 L of 5% $NaHCO_3$ and ethyl acetate was removed in vacuo. Then, the residue was dissolved in a small portion of 40% ethyl acetate/hexanes and divided into 20 separate portions. Each portion was then loaded onto a column containing 150 kg of silica gel and eluted with 40% ethyl acetate/hexanes to provide theaflavin (25 kg), theaflavin-3-gallate (9 kg), theaflavin-3'-gallate (6 kg) and theaflavin-3,3' digallate (10 kg), each as a separate compound. The theaflavins were then further purified by recrystallization from ethanol. The final purity of theaflavin, theaflavin-3-gallate, theaflavin-3'-gallate and theaflavin-3,3' digallate, as determined by HPLC was 99.1%, 98.7%, 97.8% and 99.3%, respectively. The structure of theaflavin, theaflavin-3-gallate, theaflavin-3'-gallate and theaflavin-3,3' digallate was determined by HPLC-MS.

Example 3

Preparation of Soft Gels of Theaflavins

Beeswax (2 kg) was added to olive oil (500 kg) at 80° C. with stirring for 30 minutes and cooled to 40° C. A mixture of theaflavins (100 kg), prepared via the method of Example 1, was mixed thoroughly into the above mixture of beeswax and olive oil. The resulting mixture of theaflavins, beeswax and olive oil were placed into a gel comprised of gelatin powder to prepare the soft gel capsules. Each soft gel capsule is about 700 mg of which about 75 mg are the mixture of theaflavins.

Example 4

Use of Theaflavins to Elevate Lipid Profile in Rats

Male Sprague-Dawley rats weighing 100 g to 130 g were divided into nine groups of ten rats. The animals were individually housed in stainless-steel cages with screen bottoms in a room maintained at between 22° C. and 24° C. They were fed stationary feedstuff and water as follows as described in Table 1. In addition the rats in Group TF1-1, TF1-2 or TF1-3 were fed pure theaflavin in a dosage of 1 mg/kg/day, 2 mg/kg/day and 4 mg/kg/day, respectively. The animals in group TF2A-2, TF2B-2 or RF3-2 were fed pure theaflavin-3-gallate, theaflavin-3'-gallate and theaflavin-3,3'-digallate, respectively in a dosage of 2 mg/kg/day. The animals in group CA-1 and CA-2 were fed catechins in a dosage of 1 mg/kg/day or 2 mg/kg/day, respectively.

TABLE 1

| Ingredients | | Control | TF1-1 | TF1-2 | TF1-3 | TF2A-2 | TF2B-2 | TF3-2 | CA-1 | CA-2 |
|---|---|---|---|---|---|---|---|---|---|---|
| Basic feedstuff | casein | 20% | 20% | 20% | 20% | 20% | 20% | 20% | 20% | 20% |
| | starch | 47.5% | 47% | 46% | 45% | 46% | 46% | 46% | 46% | 46% |
| | mineral | 4.5% | 4.5% | 4.5% | 4.5% | 4.5% | 4.5% | 4.5% | 4.5% | 4.5% |
| | vitamin | 1.5% | 1.5% | 1.5% | 1.5% | 1.5% | 1.5% | 1.5% | 1.5% | 1.5% |
| | sucrose | 20% | 20% | 20% | 20% | 20% | 20% | 20% | 20% | 20% |
| Corn oil | | 5% | 5% | 5% | 5% | 5% | 5% | 5% | 5% | 5% |
| Cholesterol | | 1.0% | 1.0% | 1.0% | 1.0% | 1.0% | 1.0% | 1.0% | 1.0% | 1.0% |
| mg/kg/day theaflavins | Theaflavin | — | 1 | 2 | 3 | — | — | — | — | — |
| | Theaflavin-3-gallate | — | — | — | — | 2 | — | — | — | — |
| | Theaflavin-3'-gallate | — | — | — | — | — | 2 | — | — | — |
| | Theaflavin-3,3'-digallate | — | — | — | — | — | — | 2 | — | — |
| Catechin mg/kg/day | | — | — | — | — | — | — | — | 1 | 2 |

The Sprague Dawley rats were fed the above diets for eight weeks before sampling. The rats were not fed for 12 hours prior to sampling. The rats were given either theaflavin, theaflavin-3-gallate, theaflavin-3'-gallate, theaflavin-3,3'-digallate or catechin one hour in advance of collecting the blood sample.

TABLE 2

Lipids profile of rats after taking catechin or theaflavins

| | Groups | | | | | | | | |
|---|---|---|---|---|---|---|---|---|---|
| | Control | TF1-1 | TF1-2 | TF1-3 | TF2A-2 | TF2B-2 | TF3-2 | CA-1 | CA-2 |
| TG | 120.2 ± 14.4 | 108.1 ± 13.8[2] | 97.4 ± 11.6[1] | 87.7 ± 12.2[1] | 95.7 ± 10.5[1] | 96.2 ± 10.2[1] | 95.36 ± 9.2[1] | 113.9 ± 12.0[3] | 106.7 ± 10.5[2] |
| TC | 131.3 ± 10.0 | 116.3 ± 8.2[1] | 101.3 ± 7.9[1] | 90.8 ± 7.1[1] | 97.3 ± 8.4[1] | 97.8 ± 8.5[1] | 95.5 ± 7.4[1] | 123.1 ± 8.1[3] | 113.2 ± 11.1[3] |
| LDL | 54.9 ± 3.4 | 45.6 ± 3.1[1] | 34.6 ± 3.7[1] | 25.3 ± 2.2[1] | 32.2 ± 3.7[1] | 32.4 ± 3.3[1] | 31.2 ± 4.1[1] | 49.5 ± 3.3[3] | 44.1 ± 2.43 |
| HDL | 48.3 ± 1.7 | 48.8 ± 1.7[3] | 49.2 ± 2.1[3] | 49.4 ± 1.9[3] | 49.2 ± 1.9[3] | 49.3 ± 2.7[3] | 49.3 ± 1.9[3] | 48.2 ± 2.2[3] | 48.4 ± 1.9[3] |

[1] $P < 0.01$, compared to the control group
[2] $P < 0.05$, compared to the control group
[3] There is no significant difference between the control and medicine group As shown in Table 2, the rats in the theaflavin groups had greatly decreased dose dependent plasma levels of total cholesterol ("TC"), low density lipoprotein-cholesterol ("LDL-C") and triglyceride ("TG") when compared with to the control group. Theaflavin, theaflavin-3-gallate, theaflavin-3'-gallate, theaflavin-3,3'-digallate were more effective in reducing plasma levels of TC, LDL-C and TG than catechin.

Example 5

Effect of a Mixture of Theaflavins on Subjects with Mild to Moderate Hyperlipidemia Choleve™ is a mixture of theaflavin, theaflavin-3-gallate, theaflavin-3'-gallate and theaflavin-3,3'-digallate prepared as described in Example 1. The clinical trial was a double-blind, randomized, placebo-controlled, parallel-group trial, which lasts for 12 weeks.

Patients were 19 years of age and older with mild to moderate hyperlipidemia (LDL-C 130-190 mg/dL) on a low fat diet and were recruited from outpatient clinics in six hospitals in China. Patients were excluded if their baseline triglycerides were 350 mg/dL or greater or if they had uncontrolled hypertension ($\geq 160/95$ mm Hg). Patients with active pulmonary, hematologic, hepatic, gastrointestinal or renal disease, pre-malignant or malignant disease, diabetes, thyroid dysfunction, a history of coronary heart disease or other atherosclerotic disease were also excluded. Patients with pathological values among routine clinical chemistry or hematological parameters or if they consumed >32% of daily energy from fat or had a body mass index $\geq 35$ were also excluded. Subjects were also excluded if they were taking any lipid lowering medications or drugs that might interfere with lipid metabolism, cardiac or other vasoactive medications including antihypertensive drugs, thyroid hormones, oral contraceptives, cyclic hormone replacement therapy, dietary supplements (e.g., fish oils, niacin at doses >400 mg/day, dietary fiber supplements), or antioxidants and they were prohibited from taking these medications during the course of the study. Patients were required to maintain a stable diet and level of physical activity during a 12-week study.

The inclusion and exclusion criteria were met by two hundred and forty patients. After randomization, clinic visits were scheduled in the morning of weeks 4, 8, and 12 after a 12-hour fast. Parameters measured at each visit included body weight, blood pressure and heart rate. Subjects were asked to record study capsules taken, concomitant medications, and any adverse events in subject diaries. Study capsules were dispensed at baseline, week 4, and week 8. Nutrient intake was assessed using 3-day food records completed by the subjects prior to baseline and after eight weeks of treatment. Lipid and lipoprotein concentrations were measured at week −2, week 0, week 4 and week 12. Lipids and lipoproteins were analyzed enzymatically using standard laboratory procedures. The results, which include serum chemistry and hematology tests, were tested on an automatic biochemical instrument (Sybchron Clinical System LX 20, Beckman Coulter, Inc., Shanghai Representative Office Room 3203-3205, Hong Kong Plaza, South Building, 283 Huai Hai Zhong Road, Shanghai, China 200021). Platelet aggregation was induced by adenosine diphosphate and the rate of platelet aggregation was determined by the optical density measurements at 915 mn.

Two hundred forty subjects were randomized into the study, and two hundred and twenty subjects completed the trial. The baseline characteristics are presented in Table 1. All subjects were Asian with 95% of subjects in the treatment group and 88% in the placebo group finishing the study. Fourteen subjects failed to return, five subjects were discontinued from the study at their request and one subject was terminated for protocol violation.

After four weeks and twelve weeks of oral administration of Choleve™, the serum LDL-C level in the subjects decreased by 9.6% (4.08 mmol/1-3.68 mmol/L) and 16.4% (4.08 mmol/1-3.40 mmol/1) compared to the base line at start (P=0.0001) (see Tables 3 and 4). At the same time, Choleve™ caused 6.7% and 11.3% decrease in the serum TC level (P=0.0001). On the other hand, the LDL-C and TC levels in the placebo group showed no significant changes after four weeks and twelve weeks. However, there are no significant changes in the TG and high density lipoprotein ("HDL") levels between Choleve™ and placebo group after 12 weeks treatment.

TABLE 3

Fasting serum lipid parameters (mmol/L) after 4 week and 12 weeks' treatment

| | 0 weeks | | 4 weeks | | 12 weeks | |
|---|---|---|---|---|---|---|
| | Choleve ™ (n = 114) | Placebo (n = 109) | Choleve ™ (n = 114) | Placebo (n = 109) | Choleve ™ (n = 114) | Placebo (n = 109) |
| TC | 6.31 ± 0.58 | 6.18 ± 0.64 | 5.87 ± 0.68[2,3] | 6.18 ± 0.80 | 5.58 ± 0.70[2,3] | 6.12 ± 0.64 |
| LDL-c | 4.08 ± 0.42 | 4.00 ± 0.46 | 3.68 ± 0.55[2,3] | 4.06 ± 0.65 | 3.40 ± 0.56[2,3] | 4.00 ± 0.55 |
| HDL-c[4] | 1.43 ± 0.32 | 1.45 ± 0.36 | 1.40 ± 0.32 | 1.42 ± 0.35 | 1.42 ± 0.29 | 1.41 ± 0.32 |
| TG[5] | 2.10 ± 0.86 | 1.93 ± 0.82 | 2.08 ± 0.97 | 2.00 ± 0.82 | 2.07 ± 1.02 | 1.90 ± 0.79 |

[1] T = SD
[2] P = 0.0001 compared to the baseline
[3] P - 0.001 compared to the baseline, the baseline value as covariance
[4,5] there is no significant difference between the active and placebo group

TABLE 4

Mean percent change from baseline in lipid parameters[1] ($\chi$ ± SE)

| | 4 weeks | | 12 weeks | |
|---|---|---|---|---|
| | Choleve ™ (n = 114) | Placebo (n = 109) | Choleve ™ (n = 114) | Placebo (n = 109) |
| TC (%)[2] | -6.70 ± 0.84 | 0.05 ± 0.87 | -11.34 ± 0.89 | -0.72 ± 0.77 |
| LDL-c(%)[3] | -9.58 ± 1.09 | 1.75 ± 1.29 | -16.4 ± 1.10 | 0.26 ± 1.24 |
| HDL-c(%)[4] | 0.35 ± 2.10 | -0.36 ± 1.65 | 2.30 ± 2.06 | -0.69 ± 1.59 |
| TG(%)[5] | 0.51 ± 2.58 | 11.79 ± 4.82 | 2.58 ± 3.52 | 5.58 ± 3.76 |

[1] ($\chi$ ± SEM
[2,3] P = 0.0001 compared to the baseline
[4,5] there is no significant difference between the active and placebo group Table 5 illustrate that Choleve™ had no effect to the platelet aggregation.

TABLE 5

PLAG(%) after 4 week and 12 weeks' duration

| | 4 weeks | | 12 weeks | |
|---|---|---|---|---|
| | Choleve ™ (n = 114) | Placebo (n = 109) | Choleve ™ (n = 114) | Placebo (n = 109) |
| PLAG % (1 min) | 40.2 ± 16.1 | 37.5 ± 14.0 | 36.8 ± 15.6 | 40.3 ± 16.1 |
| PLAG % (Tmax) | 56.2 ± 20.6 | 57.3 ± 19.1 | 56.5 ± 23.0 | 57.4 ± 19.1 |

After twelve weeks of oral administration of Choleve™, the extract decreased serum total cholesterol and LCL-C by 11.3% and 16.4%, respectively, as shown above, which indicates the potential of Choleve™ in treating and preventing coronary heart disease. No adverse reactions to Choleve™ occurred during this clinical trial, which demonstrates the safety of Choleve™.

What is claimed is:

1. A pharmaceutical composition comprising an isolated mixture of theaflavin, theaflavin-3-gallate, theaflavin-3'-gallate and theaflavin-3,3'-digallate or a pharmaceutically available salt, hydrate or solvate thereof and a pharmaceutically acceptable vehicle.

2. A diet supplement composition comprising an isolated mixture of theaflavin, theaflavin-3-gallate, theaflavin-3'-gallate and theaflavin-3,3'-digallate or a pharmaceutically available salt, hydrate or solvate thereof and a suitable diet supplement vehicle.

3. A method of treating or preventing coronary heart disease comprising administering to a patient in need of such treatment or prevention a therapeutically effective amount of the pharmaceutical composition of claim 1.

4. A method of treating or preventing apoplexy comprising administering to a patient in need of such treatment or prevention a therapeutically effective amount of the pharmaceutical composition of claim 1.

5. A method of treating or preventing atherosclerotic cardiovascular diseases comprising administering to a patient in need of such treatment or prevention a therapeutically effective amount of the pharmaceutical composition of claim 1.

6. A method of treating or preventing diabetes comprising administering to a patient in need of such treatment or prevention a therapeutically effective amount of the pharmaceutical composition of claim 1.

7. A method of treating or preventing increased von Willebrand's disease comprising administering to a patient in need of such treatment or prevention a therapeutically effective amount of the pharmaceutical composition of claim 1.

8. A method of treating or preventing leukopenia comprising administering to a patient in need of such treatment or prevention a therapeutically effective amount of the pharmaceutical composition of claim 1.

9. A method of treating or preventing cerebral infarction comprising administering to a patient in need of such treatment or prevention a therapeutically effective amount of the pharmaceutical composition of claim 1.

10. A method of treating or preventing dementia and physical disorder induced by cardio- and cerebral-vascular disease comprising administering to a patient in need of such treatment or prevention a therapeutically effective amount of the pharmaceutical composition of claim 1.

11. A capsule comprising a shell comprising gelatin, water and optionally a plasticizer; and a fill material comprising a mixture of theaflavin, theaflavin-3-gallate, theaflavin-3'-gallate and theaflavin-3,3'-digallate; wherein the shell or the fill material further comprises a radiation blocker and a antioxidant.

12. The capsule of claim 11, wherein the shell is a soft elastic capsule that includes the plasticizer, optionally a colorant and optionally, a radiation blocker.

13. The capsule of claim 12, wherein the plasticizer is a polyol.

14. The capsule of claim 13, wherein the plasticizer is a mixture of glycerin and sorbitol.

15. The capsule of claim 11 wherein the fill material further comprises an anti-oxidant, a pharmaceutically acceptable carrier and optionally, an emulsifier.

16. The capsule of claim 15, wherein the anti-oxidant is Vitamin E, the pharmaceutically acceptable carrier is soybean oil and the emulsifier is lecithin.

17. The capsule of claim 15, wherein the fill material further comprises a stiffening agent.

18. The capsule of claim 15, wherein the stiffening agent is beeswax.

19. The capsule of claim 11, wherein the shell includes a ultraviolet radiation blocker in an amount sufficient to prevent ultraviolet degradation of the mixture of theaflavins and the fill material includes an anti-oxidant in an amount sufficient to prevent oxidative degradation of the mixture of theaflavins.

20. The capsule of claim 12, wherein the shell comprises: between about 25% and about 45% gelatin; between about 1% and about 30% plasticizer; between about 5% and about 40% water; between about 1% and about 5% ultraviolet radiation blocker; and between about 1% to about 5% colorant.

21. The capsule of claim 15, wherein the fill material comprises: between about 1% and about 20% mixture of theaflavins; between about 1% and about 5% anti-oxidant; between about 5% and about 90% pharmaceutically acceptable carrier; between about 1% and about 20% emulsifier; and between about 1% to about 20% stiffening agent.

22. The capsule of claim 11 further comprising a masticatory substance.

23. A method of reducing low density lipoprotein (LDL) while not significantly reducing high density lipoprotein (HDL) in a human subject, which method comprises administering over time a composition comprising an isolated mixture of theaflavin, theaflavin-3-gallate, theaflavin-3'-gallate, and theaflavin 3,3'-digallate in a therapeutically effective amount and for a time period sufficient to reduce the LDL while not significantly reducing the HDL over the time of administration.

24. The method of claim 23, wherein the administration is continued for at least four weeks.

25. The method of claim 23, wherein the administration is continued for at least twelve weeks.

26. The method of claim 23, wherein the theaflavin, theaflavin-3-gallate, theaflavin-3'-gallate, and theaflavin 3,3'-digallate mixture is administered to the subject at a daily dosage rate of about 0.001 mg/kg to about 200 mg/kg body weight of the subject.

27. The method of claim 26, wherein the theaflavin, theaflavin-3-gallate, theaflavin-3'-gallate, and theaflavin 3,3'-digallate mixture is administered at the daily dosage rate of about 0.1 mg/kg to about 5 mg/kg body weight of the subject.

28. The method of claim 23, wherein the composition is an oral composition.

29. The method of claim 28, wherein the oral composition is a tablet, capsule, powder, solution, suspension, emulsion, pill, pellet, or sustained-release formulation.

30. The method of claim 28, wherein the oral composition contains the theaflavin, theaflavin-3-gallate, theaflavin-3'-gallate, and theaflavin 3,3'-digallate mixture in a purified form in combination with a pharmaceutically acceptable vehicle.

31. The method of claim 30, wherein the theaflavin, theaflavin-3-gallate, theaflavin-3'-gallate, and theaflavin 3,3'-digallate mixture is present at a level of about 5% to about 50% (w/w) of the composition administered.

32. The method of claim 23, wherein the human subject suffers from hyperlipidemia.

33. A composition suitable for oral administration to a human subject over time, which composition comprises an isolated mixture of theaflavin, theaflavin-3-gallate, theaflavin-3'-gallate, and theaflavin 3,3'-digallate in a therapeutically effective amount sufficient to reduce low density lipoprotein (LDL) while not significantly reducing high density lipoprotein (HDL), when the composition is delivered on a daily basis over time.

34. The composition of claim 33, wherein the composition comprises a tablet, capsule, powder, solution, suspension, emulsion, pill, pellet, or sustained-release formulation.

35. The composition of claim 33, wherein the theaflavin, theaflavin-3-gallate, theaflavin-3'-gallate, and theaflavin 3,3'-digallate of the composition is in purified form and is combined with a pharmaceutically acceptable vehicle.

36. The composition of claim 35, wherein the theaflavin, theaflavin-3-gallate, theaflavin-3'-gallate, and theaflavin 3,3'-digallate of the composition is present at a level of about 5% to about 50% (w/w) of the dosage form.

37. The composition of claim 33, wherein the mixture is combined with an oil.

38. The composition of claim 37, wherein the mixture is combined with vegetable oil.

39. The composition of claim 38, wherein the mixture is combined with vegetable oil encapsulated in a capsule.

40. The composition of claim 38, wherein the vegetable oil comprises corn oil, peanut oil, safflower oil, sunflower oil, soybean oil or a combination thereof.

41. The composition of claim 33, wherein the composition is to be administered for at least 4 weeks.

42. The composition of claim 33, wherein the composition is to be administered for at least 12 weeks.

43. The composition of claim 33, wherein the composition is for administration to a human subject that exhibits hyperlipidemia.

44. The method of claim 23, wherein the theaflavin, theaflavin-3-gallate, theaflavin-3'-gallate, and theaflavin 3,3'-digallate mixture is administered to the subject at a daily dose of between about 70 mg to about 210 mg.

45. The method of claim 29, wherein said capsule comprises a soft gel capsule or a capsule containing a liquid.

46. The method of claim 30, wherein said pharmaceutically acceptable vehicle comprises a liquid vehicle, an excipient, an agent or a combination thereof.

47. The method of claim 46, wherein said liquid vehicle comprises water, saline solution, aqueous dextrose, glycerol solutions or a combination thereof.

48. The method of claim 46, wherein said excipient comprises starch, glucose, lactose, sucrose, gelatin, malt, rice, flour, chalk, silica gel, sodium stearate, glycerol monostearate, talc, sodium chloride, dried skim milk, glycerol, propylene, glycol, ethanol or a combination thereof.

49. The method of claim 46, wherein said agent comprises a wetting agent, a stabilizing agent, an emulsifying agent, a pH buffering agent, a thickening agent, a lubricating agent, a coloring agent or a combination thereof.

50. The method of claim 23, wherein the composition comprises between about 40% to about 50% theaflavin, between about 15% to about 25% theaflavin-3-gallate, between about 10% to about 14% theaflavin-3'-gallate, and between about 15% to about 25% theaflavin 3,3'-digallate mixture in purified form.

51. The method of claim 30, wherein the oral composition comprises between about 40% to about 50% theaflavin, between about 15% to about 25% theaflavin-3-gallate, between about 10% to about 14% theaflavin-3'-gallate, and between about 15% to about 25% theaflavin 3,3'-digallate mixture in purified form.

52. The composition of claim 33, wherein the theaflavin, theaflavin-3-gallate, theaflavin-3'-gallate, and theaflavin 3,3'-digallate mixture is a daily dose of between about 70 mg to about 210 mg.

53. The composition of claim 34, wherein said capsule comprises a soft gel capsule or a capsule containing a liquid.

54. The composition of claim 35, wherein said pharmaceutically acceptable vehicle comprises a liquid vehicle, an excipient, an agent or a combination thereof.

55. The composition of claim 54, wherein said liquid vehicle comprises water, saline solution, aqueous dextrose, glycerol solutions or a combination thereof.

56. The composition of claim 54, wherein said excipient comprises starch, glucose, lactose, sucrose, gelatin, malt, rice, flour, chalk, silica gel, sodium stearate, glycerol monostearate, talc, sodium chloride, dried skim milk, glycerol, propylene, glycol, ethanol or a combination thereof.

57. The composition of claim 54, wherein said agent comprises a wetting agent, a stabilizing agent, an emulsifying agent, a pH buffering agent, a thickening agent, a lubricating agent, a coloring agent or a combination thereof.

58. The composition of claim 33, wherein the composition comprises between about 40% to about 50% theaflavin, between about 15% to about 25% theaflavin-3-gallate, between about 10% to about 14% theaflavin-3'-gallate, and between about 15% to about 25% theaflavin 3,3'-digallate mixture in purified form.

59. The composition of claim 54, wherein the composition comprises between about 40% to about 50% theaflavin, between about 15% to about 25% theaflavin-3-gallate, between about 10% to about 14% theaflavin-3'-gallate, and between about 15% to about 25% theaflavin 3,3'-digallate mixture in purified form.

60. A method of reducing low density lipoprotein (LDL) while not significantly reducing high density lipoprotein (HDL) in a human subject, which method comprises administering over time a composition comprising an isolated mixture of theaflavin, theaflavin-3-gallate, theaflavin-3'-gallate, and theaflavin 3,3'-digallate and at least one pharmaceutically acceptable vehicle and agent in a pharmaceutically effective amount and for a time period sufficient to reduce the LDL while not significantly reducing the HDL over the time of administration.

61. The method of claim 60, wherein the administration is continued for at least four weeks.

62. The method of claim 60, wherein the administration is continued for at least twelve weeks.

63. The method of claim 60, wherein the theaflavin, theaflavin-3-gallate, theaflavin-3'-gallate, and theaflavin 3,3'-digallate mixture is administered to the subject at a daily dosage rate of about 0.001 mg/kg to about 200 mg/kg body weight of the subject.

64. The method of claim 63, wherein the theaflavin, theaflavin-3-gallate, theaflavin-3'-gallate, and theaflavin 3,3'-digallate mixture is administered at the daily dosage rate of about 0.1 mg/kg to about 5 mg/kg body weight of the subject.

65. The method of claim 60, wherein the composition is an oral composition.

66. The method of claim 65, wherein the oral composition is a tablet, capsule, powder, solution, suspension, emulsion, pill, pellet, or sustained-release formulation.

67. The method of claim 66, wherein said capsule comprises a soft gel capsule or a capsule containing a liquid.

68. The method of claim 60, wherein said pharmaceutically acceptable vehicle comprises a liquid vehicle, an excipient, an agent or a combination thereof.

69. The method of claim 68 wherein said liquid vehicle comprises water, saline solution, aqueous dextrose, glycerol solutions or a combination thereof.

70. The method of claim 68 wherein said excipient comprises starch, glucose, lactose, sucrose, gelatin, malt, rice, flour, chalk, silica gel, sodium stearate, glycerol monostearate, talc, sodium chloride, dried skim milk, glycerol, propylene, glycol, ethanol or a combination thereof.

71. The method of claim 68 wherein said agent comprises a wetting agent, a stabilizing agent, an emulsifying agent, a pH buffering agent, a thickening agent, a lubricating agent, a coloring agent or a combination thereof.

72. The method of claim 60, wherein the theaflavin, theaflavin-3-gallate, theaflavin-3'-gallate, and theaflavin 3,3'-digallate mixture is present at a level of about 5% to about 50% (w/w) of the composition administered.

73. The method of claim 60, wherein the composition comprises between about 40% to about 50% theaflavin, between about 15% to about 25% theaflavin-3-gallate, between about 10% to about 14% theaflavin-3'-gallate, and between about 15% to about 25% theaflavin 3,3'-digallate mixture in purified form.

74. The method of claim 60, wherein the human subject suffers from hyperlipidemia.

75. A method, comprising:
    administering to a human a composition comprising a shell and a mixture of theaflavin, theaflavin-3-gallate, theaflavin-3'-gallate, and theaflavin 3,3'-digallate formulated to reduce the LDL while not significantly reducing the HDL in the human.

76. The method of claim 75, wherein the shell defines an interior and the mixture is disposed within the interior of the shell.

77. The method of claim 75, wherein the mixture is an isolated mixture of theaflavin, theaflavin-3-gallate, theaflavin-3'-gallate, and theaflavin 3,3'-digallate.

78. The method of claim 77, wherein the mixture comprises between about 40% to about 50% theaflavin, between about 15% to about 25% theaflavin-3-gallate, between about 10% to about 14% theaflavin-3'-gallate, and between about 15% to about 25% theaflavin 3,3'-digallate mixture in purified form.

79. A method, comprising:
    administering to a human a composition comprising a mixture of theaflavin, theaflavin-3-gallate, theaflavin-3'-gallate, and theaflavin 3,3'-digallate formulated to reduce the LDL while not significantly reducing the HDL in the human, a weight of the mixture of theaflavin, theaflavin-3-gallate, theaflavin-3'-gallate, and theaflavin 3,3'-digallate being at least 5% of a weight of the composition.

80. The method of claim 79, wherein the weight of the theaflavin, theaflavin-3-gallate, theaflavin-3'-gallate, and theaflavin 3,3'-digallate is at least 15% of the weight of the composition.

81. The method of claim 79, wherein the weight of the theaflavin, theaflavin-3-gallate, theaflavin-3'-gallate, and theaflavin 3,3'-digallate is between 5% and 50% of the weight of the composition.

82. A composition suitable for oral administration to a human subject over time, which composition comprises an isolated mixture of theaflavin, theaflavin-3-gallate, theaflavin-3'-gallate, and theaflavin 3,3'-digallate and at least one pharmaceutically acceptable vehicle and agent in a therapeutically effective amount sufficient to reduce low density lipoprotein (LDL) while not significantly reducing high density lipoprotein (HDL), when the composition is delivered on a daily basis over time.

83. The composition of claim 82, wherein the weight of the mixture being at least 5% of a weight of the composition.

84. The composition of claim 82, wherein the weight of the mixture is at least 15% of the weight of the composition.

85. The composition of claim 82, wherein the weight of the mixture is between 5% and 50% of the weight of the composition.

86. The composition of claim 82, wherein the mixture is an isolated mixture of theaflavin, theaflavin-3-gallate, theaflavin-3'-gallate, and theaflavin 3,3'-digallate.

87. The composition of claim 82, further comprising:
a shell, the mixture begin disposed within the shell.

* * * * *